(12) United States Patent
Ignatyev et al.

(10) Patent No.: US 8,101,749 B2
(45) Date of Patent: Jan. 24, 2012

(54) PROCESS FOR THE PREPARATION OF ONIUM SALTS WITH A TETRAFLUOROBORATE ANION HAVING A REDUCED HALIDE CONTENT

(75) Inventors: Nikolai (Mykola) Ignatyev, Duisburg (DE); Urs Welz-Biermann, Heppenheim (DE); Andriy Kucheryna, Kiev (UA); Helge Willner, Muelheim/Ruhr (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 1077 days.

(21) Appl. No.: 11/721,613

(22) PCT Filed: Nov. 18, 2005

(86) PCT No.: PCT/EP2005/012398
§ 371 (c)(1),
(2), (4) Date: Jun. 13, 2007

(87) PCT Pub. No.: WO2006/063653
PCT Pub. Date: Jun. 22, 2006

(65) Prior Publication Data
US 2009/0253912 A1    Oct. 8, 2009

(30) Foreign Application Priority Data

Dec. 14, 2004  (DE) .......................... 10 2004 060 073
Jul. 27, 2005  (DE) .......................... 10 2005 035 103

(51) Int. Cl.
| | |
|---|---|
| C07D 207/04 | (2006.01) |
| C07D 231/06 | (2006.01) |
| C07D 231/10 | (2006.01) |
| C07D 233/04 | (2006.01) |
| C07D 233/54 | (2006.01) |
| C07D 249/04 | (2006.01) |
| C07D 249/08 | (2006.01) |
| C07D 263/30 | (2006.01) |
| C07D 277/20 | (2006.01) |
| C07D 215/02 | (2006.01) |
| C07D 217/02 | (2006.01) |
| C07D 211/80 | (2006.01) |
| C07D 211/06 | (2006.01) |
| C07D 209/04 | (2006.01) |
| C07D 237/06 | (2006.01) |
| C07D 239/24 | (2006.01) |
| C07D 241/10 | (2006.01) |
| C07D 241/36 | (2006.01) |

(52) U.S. Cl. ........ 544/106; 544/238; 544/353; 544/242; 546/139; 546/152; 546/347; 548/335.1; 548/347.1; 548/373.1; 548/379.1; 548/262.2; 548/400; 548/469; 548/235; 548/202

(58) Field of Classification Search .................. None
See application file for complete search history.

(56) References Cited

U.S. PATENT DOCUMENTS

| | | |
|---|---|---|
| 6,245,918 B1 | 6/2001 | Olivier et al. |
| 2003/0080312 A1 | 5/2003 | Seddon et al. |
| 2008/0027230 A1* | 1/2008 | Ignatyev et al. ............. 546/348 |

FOREIGN PATENT DOCUMENTS

EP          1 182 197 A          2/2002

OTHER PUBLICATIONS

Holderberg A W et al., Electrophile Induced Addition Reactons of Bis-phosphonio-isophosphin Dolide Cations, Tetrahedron, Jan. 2000, pp. 57-62, ISSN: 0040-4020, Elsevier Science Publishers, Amsterdam, NL.

* cited by examiner

*Primary Examiner* — Yong Chu
*Assistant Examiner* — Michael Barker
(74) *Attorney, Agent, or Firm* — Millen, White, Zelano & Branigan, P.C.

(57) ABSTRACT

The invention relates to a method for producing onium salts with tetrafluoroborate anion by reacting an onium halide with an oxonium tetrafluoroborate, sulfonium tetrafluoroborate, or triphenylcarbonium tetrafluoroborate.

3 Claims, No Drawings

PROCESS FOR THE PREPARATION OF ONIUM SALTS WITH A TETRAFLUOROBORATE ANION HAVING A REDUCED HALIDE CONTENT

The invention relates to a process for the preparation of onium salts with a tetrafluoroborate anion by reaction of an onium halide with an oxonium tetrafluoroborate, sulfonium tetrafluoroborate or triphenylcarbonium tetrafluoroborate.

A large number of onium salts are ionic liquids. Owing to their properties, ionic liquids represent an effective alternative to traditional volatile organic solvents for organic synthesis in modern research. The use of ionic liquids as novel reaction medium could furthermore be a practical solution both for solvent emission and also for problems in the reprocessing of catalysts (R. Sheldon "Catalytic reactions in ionic liquids", Chem. Commun., 2001, 2399-2407; M J. Earle, K. R. Seddon 2Ionic liquids. Green solvent for the future", Pure Appl. Chem., 72 (2000), 1391-1398; P. Wasserscheid, W. Keim "Ionische Flüssigkeiten—neue Lösungen für die Übergangsmetalikatalyse" [Ionic liquids—novel solutions for transition-metal catalysis], Angew. Chem., 112 (2000), 3926-3945; T. Welton "Room temperature ionic liquids. Solvents for synthesis and catalysis", Chem. Rev., 92 (1999), 2071-2083 or R. Hagiwara, Ya. Ito "Room temperature ionic liquids of alkylimidazolium cations and fluoroanions", J. Fluorine Chem., 105 (2000), 221-227).

Ionic liquids or liquid salts are ionic species which consist of an organic cation and a generally inorganic anion. They do not contain any neutral molecules and usually have melting points below 373 K. However, the melting point may also be higher without restricting the usability of the salts in all areas of application. Examples of organic cations are, inter alia, tetraalkylammonium, tetraalkylphosphonium, N-alkylpyridinium, 1,3-dialkylimidazolium or trialkylsulfonium. Amongst a multiplicity of suitable anions, mention may be made, for example, of $BF_4^-$, $PF_6^-$, $SbF_6^-$, $NO_3^-$, $CF_3SO_3^-$, $(CF_3SO_2)_2N^-$, $arylSO_3^-$, $CF_3CO_2^-$, $CH_3CO_2^-$ or $Al_2Cl_7^-$.

The properties of ionic liquids, for example the melting point, the thermal and electrochemical stability or viscosity, are determined by the choice of the cations and anions. Ionic liquids are non-volatile materials and therefore cannot be purified by conventional methods of purification, such as, for example, distillation, since they were developed for most organic solvents.

The technology is therefore of crucial importance in processes for the preparation of onium salts, in particular ionic liquids with a tetrafluoroborate anion, in order that these can be synthesised with low impurity levels through the reaction per se or through the reaction procedure. An impurity which is predominantly present in known ionic liquids are halide ions. If the proportion of halide ions, for example chloride ions, is greater than 1000 ppm (0.1%), the usability of the ionic liquid is reduced, in particular in the application for electrochemical processes.

The object of the present invention was accordingly to provide an alternative process for the preparation of onium tetrafluoroborates having a low chloride content which results in products of high purity in good yield and is also suitable for large-scale industrial production.

The object is achieved by the process according to the invention. The invention accordingly relates to a process for the preparation of onium tetrafluoroborates by reaction of an onium halide with a trialkyloxonium tetrafluoroborate, sulfonium tetrafluoroborate or triphenylcarbonium tetrafluoroborate.

The process according to the invention is an improvement of the known synthetic processes for onium tetrafluoroborates, which are generally 2-step processes, as described in P. Wasserscheid and W. Keim, Angew. Chem. 112 (2000), 3926-3945. In the first step of the known processes, an organic base, typically an amine, phosphine or a heterocyclic compound, is alkylated using an alkyl halide, and the resultant onium halide is converted into the tetrafluoroborate in the second step via anion exchange.

In the second step, the halide, for example 1-ethyl-3-methylimidazolium chloride or bromide, is reacted with $NaBF_4$ in acetone by the method of S. Park and R. J. Kazlauskas, J. Organic Chemistry, 66 (2001), 8395-8401, with $NaBF_4$ in water by the method of R. Karmakar and A. Samanta, J. Phys. Chem. A, 106 (2002), 6670-6675, with $AgBF_4$ or $HBF_4$ in water by the method of J. D. Holbrey and K. R. Seddon, J. Chem. Soc., Dalton Trans., (1999), 2133-2139, with $NH_4BF_4$ in acetone by the method of J. Fuller et al, J. Electrochem. Soc., 144 (1997), 3881-3885, with $HBF_4$ in methanol by the method of T. Nishida et al, J. of Fluorine Chem., 120 (2003), 135-141 or with $NH_4BF_4$ with microwave irradiation by the method of V. V. Namboodiri and R. S. Varma, Tetrahedron Lett., 43 (2002), 5381-5383.

All known processes have a disadvantage, in particular for large-scale industrial synthesis. For example, silver tetrafluoroborate is an expensive reagent. The reactions with $NaBF_4$, $NH_4BF_4$ and $HBF_4$ in water require a purification step, possibly using $AgBF_4$ or adsorbents. $HBF_4$ in methanol is not commercially available and is more expensive than aqueous $HBF_4$, which is in turn commercially available. In the reaction in aqueous $HBF_4$, however, the hydrohalic acid is formed as by-product, which cannot be removed from the end product by distillation since two salts and two acids are in equilibrium in water. The onium tetrafluoroborates obtained inevitably always contain a few percent of halide ions, documented by investigations by N. M. M Mateus et al, Green Chemistry, 5 (2003), 347-352.

Surprisingly, a simple process has been developed. In the reaction of an onium halide, for example a chloride, bromide or iodide, with an oxonium tetrafluoroborate, for example Meerwein salt, with a sulfonium tetrafluoroborate or triphenylcarbonium tetrafluoroborate, onium tetrafluoroborates and alkyl halides or triphenyl halides and dialkyl ethers or dialkyl sulfides are therefore formed as by-products, which are either gases or readily volatile compounds and can be removed from the reaction mixture without major process-engineering measures. Some of these by-products are themselves valuable materials for organic syntheses.

The process according to the invention allows the synthesis of a multiplicity of tetrafluoroborate salts, where various substituents, for example alkyl groups, may be present on the onium cation, so-called asymmetric compounds. The novel method can, however, also be used for the purification of tetrafluoroborates which contain chloride, bromide or iodide anions as impurities. Ionic liquids with tetrafluoroborate anions are thus obtained in high quality without the use of expensive materials, such as silver tetrafluoroborate, or without impurities of silver cations.

Suitable onium halides in the case of reaction with trialkyloxonium tetrad fluoroborate or triphenylcarbonium tetrafluoroborate are phosphonium halides, thiouronium halides, guanidinium halides or halides with a heterocyclic cation or in the case of reaction with trialkylsulfonium tetrafluoroborate are ammonium halides, phosphonium halides, thiouronium halides, guanidinium halides or halides with a heterocyclic cation, where the halides can be selected from the group chlorides, bromides or iodides. Chlorides or bromides are preferably employed in the process according to the invention. Thiouronium iodides are preferably employed in the process according to the invention for the class of the thiouronium salts.

The onium halides are generally commercially available or can be prepared by synthetic methods as known from the literature, for example in the standard works, such as Houben-Weyl, Methoden der organischen Chemie [Methods of Organic Chemistry], Georg-Thieme-Verlag, Stuttgart or Richard C. Larock, Comprehensive Organic Transformations, 2nd Edition, Wiley-VCH, New York, 1999. Use can also be made here of variants known per se which are not mentioned here in greater detail.

Onium halides, as described above or below, are preferably employed in the process according to the invention.

Phosphonium halides can be described, for example, by the formula (1)

[XR$_4$]$^+$Hal$^-$ (1), where
X denotes N, P
Hal denotes Cl, Br or I and
R in each case, independently of one another, denotes
H, where all substituents R cannot simultaneously be H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or more R may be partially or fully substituted by F, but where all four or three R must not be fully substituted by F,
and where, in the R, one or two non-adjacent carbon atoms which are not in the α- or ω-position may be replaced by atoms and/or atom groups selected from the group —O—, —S—, —S(O)— or —SO$_2$—.

However, compounds of the formula (1) in which all four or three substituents R are fully substituted by halogens, for example tris(trifluoromethyl)-methylammonium chloride, tetra(trifluoromethyl)ammonium chloride or tetra(nonafluorobutyl)ammonium chloride, tris(trifluoromethyl)methylphosphonium chloride, tetra(trifluoromethyl)phosphonium chloride or tetra(nonafluorobutyl)phosphonium chloride, are excluded.

Thiouronium halides can be described, for example, by the formula (2)

[(R$^1$R$^2$N)—C(=SR$^7$)(NR$^3$R$^4$)]$^+$Hal$^-$ (2)

and guanidinium halides can be described, for example, by the formula (3)

[C(NR$^1$R$^2$)(NR$^3$R$^4$)(NR$^5$R$^6$)]$^+$Hal$^-$ (3), where
Hal in formula (2) denotes Br or I and in formula (1) denotes, Cl, Br or I, and
R$^1$ to R$^7$ each, independently of one another, denotes hydrogen or CN, where hydrogen is excluded for R$^7$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more of the substituents R$^1$ to R$^7$ may be partially or fully substituted by F, but where all substituents on an N atom must not be fully substituted by F,
where the substituents R$^1$ to R$^7$ may be connected to one another in pairs by a single or double bond
and where, in the substituents R$^1$ to R$^6$, one or two non-adjacent carbon atoms which are not bonded directly to the heteroatom and are not in the ω-position may be replaced by atoms and/or atom groups selected from the group —O—, —S—, —S(O)— or —SO$_2$—.

Halides with a heterocyclic cation can be described, for example, by the formula (4)

[HetN]$^+$Hal$^-$ (4), where
Hal denotes Cl, Br or I and
HetN$^+$ denotes a heterocyclic cation selected from the group

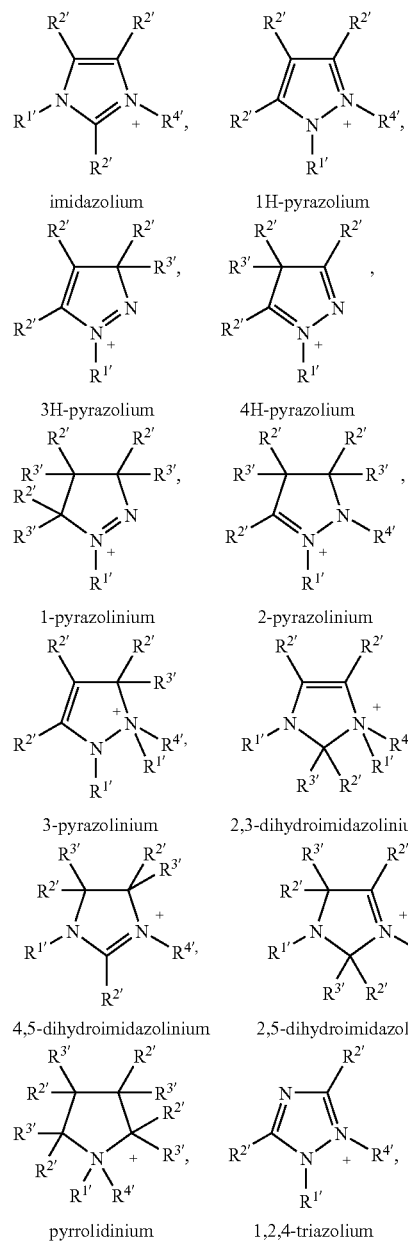

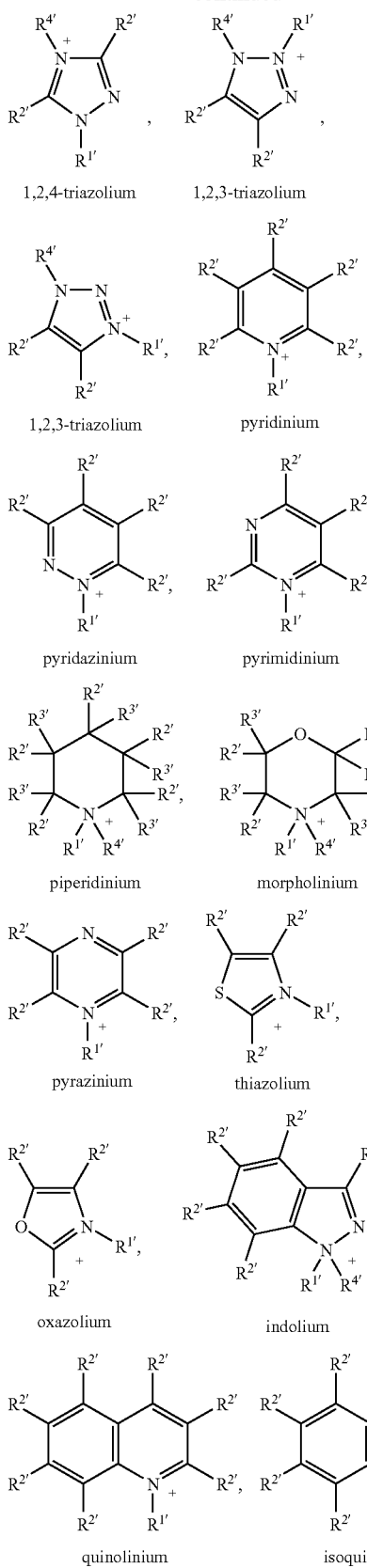
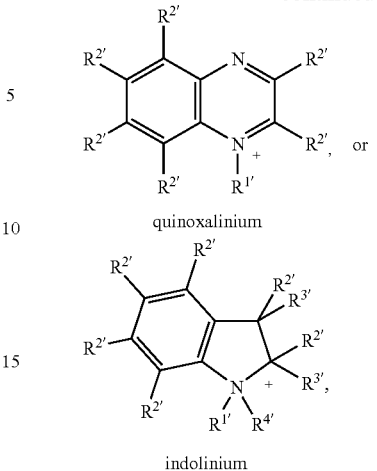

where the substituents
$R^{1'}$ to $R^{4'}$ each, independently of one another, denotes hydrogen or CN,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
dialkylamino having alkyl groups having 1-4 C atoms, but which is not bonded to the heteroatom of the heterocycle,
saturated, partially or fully unsaturated cycloalkyl having 3-7 C atoms, which may be substituted by alkyl groups having 1-6 C atoms, or aryl-$C_1$-$C_6$-alkyl,
where the substituents $R^{1'}$ and $R^{4'}$ may be partially or fully substituted by F, but where $R^{1'}$ and $R^{4'}$ are not simultaneously CN or must not simultaneously be fully substituted by F,
where the substituents $R^{2'}$ and $R^{3'}$ may be partially or fully substituted by halogens or partially by $NO_2$ or CN,
and where, in the substituents $R^{1'}$ to $R^{4'}$, one or two non-adjacent carbon atoms which are not bonded directly to the heteroatom and are not in the ω-position may be replaced by atoms and/or atom groups selected from the group —O—, —S—, —S(O)— or —$SO_2$—.

For the purposes of the present invention, fully unsaturated substituents are also taken to mean aromatic substituents.

In accordance with the invention, suitable substituents R and $R^1$ to $R^7$ of the compounds of the formulae (1) to (3), besides hydrogen, are preferably: $C_1$- to $C_{20}$-, in particular $C_1$- to $C_{14}$-alkyl groups, and saturated or unsaturated, i.e. also aromatic, $C_3$- to $C_7$-cycloalkyl groups, which may be substituted by $C_1$- to $C_6$-alkyl groups, in particular phenyl. However, the substituents R and $R^1$ to $R^7$ may likewise be substituted by further functional groups, for example by CN, $SO_2R'$, $SO_2OR'$ or COOR'. R' denotes non-, partially or perfluorinated $C_1$- to $C_6$-alkyl, $C_3$- to $C_7$-cycloalkyl, unsubstituted or substituted phenyl.

The substituents R in the compounds of the formula (1) may be identical or different here. Preferably, three substituents in formula (1) are identical and one substituent is different.

The substituent R is particularly preferably methyl, ethyl, isopropyl, propyl, butyl, sec-butyl, pentyl, hexyl, octyl, decyl or tetradecyl.

Up to four substituents of the guanidinium cation may also be connected in pairs in such a way that mono-, bi- or polycyclic cations are formed. Without restricting generality, examples of such guanidinium cations are:

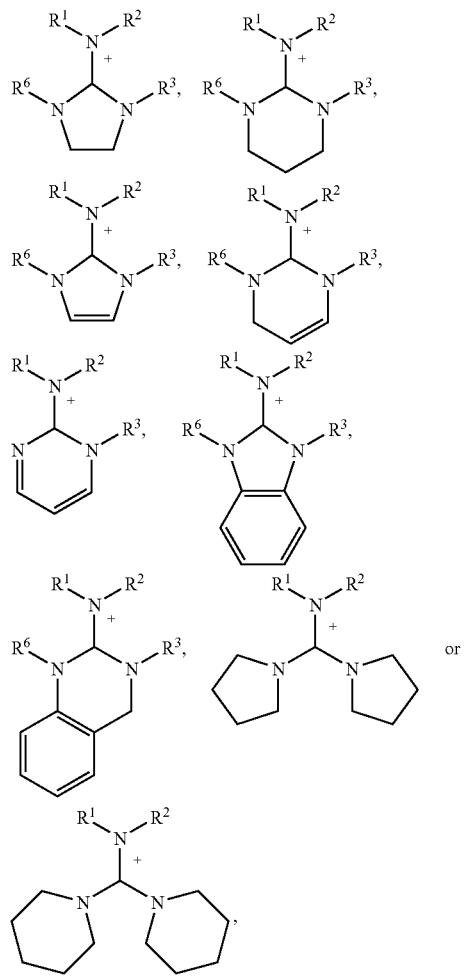

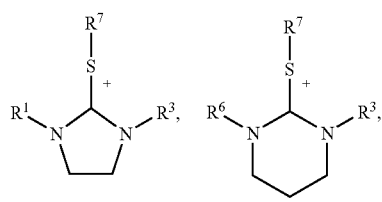

where the substituents $R^1$ to $R^3$ and $R^6$ can have an above-mentioned or particularly preferred meaning.

The carbocycles or heterocycles of the above-mentioned guanidinium cations may optionally also be substituted by $C_1$- to $C_6$-alkyl, $C_1$- to $C_6$-alkenyl, $NO_2$, F, Cl, Br, I, $C_1$-$C_6$-alkoxy, $SCF_3$, $SO_2CH_3$, $SO_2CF_3$, COOR'', $SO_2NR''_2$, $SO_2X'$, $SO_3R''$, substituted or unsubstituted phenyl, where X' and R'' have a meaning indicated above or below, Up to four substituents of the thiouronium cation $[(R^1R^2N)-C(=SR^7)-(NR^3R^4)]^+$ may also be connected in pairs in such a way that mono-, bi- or polycyclic cations are formed.

Without restricting generality, examples of such cations are indicated below:

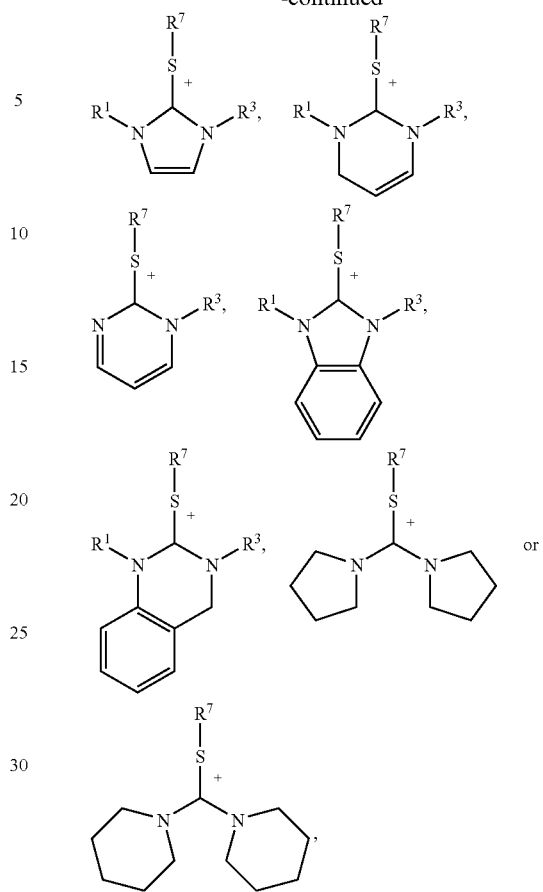

where the substituents $R^1$, $R^3$ and $R^7$ can have an above-mentioned or particularly preferred meaning.

The carbocycles or heterocycles of the above-mentioned guanidinium cations may optionally also be substituted by $C_1$ to $C_6$-alkyl, $C_1$- to $C_6$-alkenyl, $NO_2$, F, Cl, Br, I, $C_1$-$C_6$-alkoxy, $SCF_3$, $SO_2CH_3$, $SO_2CF_3$, COOR'', $SO_2NR''_2$, $SO_2X'$, $SO_3R''$, substituted or unsubstituted phenyl, where X' and R'' have a meaning indicated above or below.

The $C_1$-$C_{14}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl, dodecyl tridecyl or tetradecyl, optionally perfluorinated, for example as difluoromethyl, trifluoromethyl, pentafluoroethyl, heptafluoropropyl or nonafluorobutyl.

A straight-chain or branched alkenyl having 2 to 20 C atoms, where a plurality of double bonds may also be present, is, for example, vinyl, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$, preferably allyl, 2- or 3-butenyl, isobutenyl, sec-butenyl, furthermore preferably 4-pentenylt, isopentenyl or hexenyl.

A straight-chain or branched alkynyl having 2 to 20 C atoms, where a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

Aryl-$C_1$-$C_6$-alkyl denotes, for example, benzyl, phenylethyl, phenylpropyl, phenylbutyl, phenylpentyl or phenyl-hexyl, where both the phenyl ring and also the alkylene chain may be partially or fully substituted as described above by F, particularly preferably benzyl or phenylpropyl.

However, the phenyl ring or also the alkylene chain may likewise be substituted by further functional groups, for example by CN, $SO_2R'$, $SO_2OR'$ or $COOR'$. R' here has a meaning defined above.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups, where the cycloalkyl group or the $C_1$- to $C_6$-alkyl-substituted cycloalkyl group may in turn also be substituted by halogen atoms, such as F, Cl, Br or I, in particular F or Cl, or $NO_2$. However, the cycloalkyl groups may likewise be substituted by further functional groups, for example by CN, $SO_2R'$, $SO_2OR'$ or $COOR'$, R' here has a meaning defined above.

In the substituents R, $R^1$ to $R^6$ or $R^{1'}$ to $R^{4'}$, one or two non-adjacent carbon atoms which are not bonded in the α-position to the heteroatom or in the ω-position may also be replaced by atoms and/or atom groups selected from the group —O—, —S—, —S(O)— or —$SO_2$—.

Without restricting generality, examples of substituents R, $R^1$ to $R^6$ and $R^{1'}$ to $R^{4'}$ modified in this way are:
—$OCH_3$, —$OCH(CH_3)_2$, —$CH_2OCH_3$, —$CH_2$—$CH_2$—O—$CH_3$, —$C_2H_4OCH(CH_3)_2$, —$C_2H_4SC_2H_5$, —$C_2H_4SCH(CH_3)_2$, —$S(O)CH_3$, —$SO_2CH_3$, —$SO_2C_6H_5$, —$SO_2C_3H_7$, —$SO_2CH(CH_3)_2$, —$SO_2CH_2CF_3$, —$CH_2SO_2CH_3$, —O—$C_4H_8$—O—$C_4H_9$, —$CF_3$, —$C_2F_5$, —$C_3F_7$—$C_4F_9$, —$CF_2CF_2H$, —$CF_2CHFCF_3$, —$CF_2CH(CF_3)_2$, —$C_2F_4N(C_2F_5)C_2F_5$, —$CHF_2$—$C_2HCF_3$, —$C_2F_2H_3$, —$C_3FH_6$, —$CH_2C_3F_7$, —$CH_2C(O)OCH_3$, —$CH_2C_6H_5$ or —$C(O)C_6H_5$.

In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, $NO_2$, F, Cl, Br, I, $C_1$-$C_6$-alkoxy, $SCF_3$, $SO_2CH_3$, $SO_2CF_3$, $COOR''$, $SO_2X'$, $SO_2NR''_2$ or $SO_3R''$, where X' denotes F, Cl or Br and R'' denotes a non- or partially fluorinated $C_1$- to $C_6$-alkyl or $C_3$- to $C_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethylphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

The substituents $R^1$ to $R^7$ are each, independently of one another, preferably a straight-chain or branched alkyl group having 1 to 10 C atoms. The substituents $R^1$ and $R^2$, $R^3$ and $R^4$ and $R^5$ and $R^6$ in compounds of the formulae (2) and (3) may be identical or different here.

$R^1$ to $R^7$ are particularly preferably each, independently of one another, methyl, ethyl, n-propyl, isopropyl, n-butyl, sec-butyl, phenyl or cyclohexyl, very particularly preferably methyl, ethyl, n-propyl, isopropyl or n-butyl.

In accordance with the invention, suitable substituents $R^{1'}$ to $R^{4'}$ of compounds of the formula (4), besides hydrogen, are preferably. CN, $C_1$- to $C_{20}$-, in particular $C_1$- to $C_{12}$-alkyl groups, and saturated or unsaturated, i.e. also aromatic, $C_3$- to $C_7$-cycloalkyl groups, which may be substituted by $C_1$- to $C_6$-alkyl groups, in particular phenyl or aryl-$C_1$-$C_6$-alkyl or diaminoalkyl having $C_1$-$C_4$-alkyl groups, so long as this is not bonded to the heteroatom. However, the substituents $R^{1'}$ to $R^{4'}$ may likewise be substituted by further functional groups, for example by CN, $SO_2R'$, $SO_2OR'$ or $COOR'$. R' denotes non-, partially or perfluorinated $C_1$- to $C_6$-alkyl, $C_3$- to $C_7$-cycloalkyl, unsubstituted or substituted phenyl.

The substituents $R^{1'}$ and $R^{4'}$ are each, independently of one another, particularly preferably CN, methyl, ethyl, isopropyl, propyl, butyl, sec-butyl, pentyl, hexyl, octyl, decyl, cyclohexyl, phenyl, phenylpropyl or benzyl. They are very particularly preferably CN, methyl, ethyl, n-butyl or hexyl. In pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular hydrogen, methyl, ethyl, isopropyl, propyl, butyl, sec-butyl, tert-butyl, cyclohexyl, dimethylamino, diethylamino, methylethylamino, phenyl or benzyl, $R^{2'}$ is particularly preferably dimethylamino, hydrogen, methyl, ethyl, isopropyl, propyl, butyl, sec-butyl or tert-butyl. $R^{2'}$ and $R^{3'}$ are very particularly preferably hydrogen, dimethylamino or methyl.

HetN$^+$ of the formula (4) is preferably

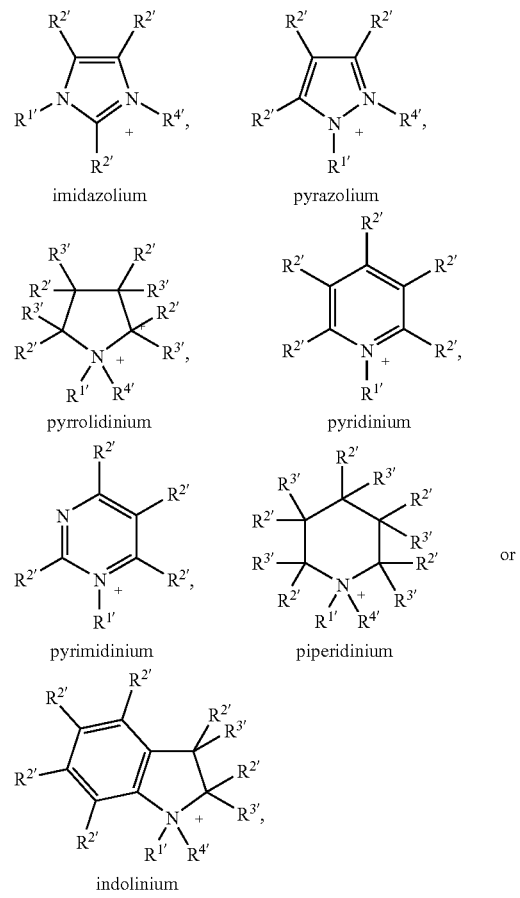

where the substituents $R^{1'}$ to $R^{4'}$ each, independently of one another, have a meaning described above.

HetN[+] is particularly preferably imidazolium, pyrrolidinium or pyridinium, as defined above, where the substituents $R^{1'}$ to $R^{4'}$ each, independently of one another, have a meaning described above.

The oxonium tetrafluoroborate having the formula $[(alkyl)_3O]^+ [BF_4]^-$ employed is preferably an oxonium tetrafluoroborate having straight-chain or branched alkyl groups having 1-8 C atoms, preferably having 1-4 C atoms, which are in each case independent of one another. Preference is given to the use of oxonium tetrafluoroborates in which the alkyl groups are identical. It is also possible to use tritylium tetrafluoroborate, $[(phenyl)_3C]^+ [BF_4]^-$.

The sulfonium tetrafluoroborate having the formula $[(alkyl)_3S]^+ [BF_4]^-$ employed is preferably a sulfonium tetrafluoroborate having straight-chain or branched alkyl groups having 1-8 C atoms, preferably having 1-4 C atoms, which are in each case independent of one another. Preference is given to the use of sulfonium tetrafluoroborates in which the alkyl groups are identical.

The oxonium tetrafluoroborates or sulfonium tetrafluoroborates employed are generally commercially available or can be prepared by synthetic methods as known from the literature, for example in the standard works, such as Houben-Weyl, Methoden der organischen Chemie [Methods of Organic Chemistry], Georg-Thieme-Verlag, Stuttgart, or Richard C. Larock, Comprehensive Organic Transformations, 2nd Edition, Wiley-VCH, New York, 1999. Use can also be made here of variants known per se which are not mentioned here in greater detail.

Examples of oxonium tetrafluoroborates are trimethyloxonium tetrafluoroborate, triethyloxonium tetrafluoroborate (Meerwein salt), tris(n-propyl)oxonium tetrafluoroborate, dimethylethyloxonium tetrafluoroborate, diethylmethyloxonium tetrafluoroborate or tris(i-propyl)oxonium tetrafluoroborate. Very particular preference is given to the use of trimethyl- or triethyloxonium tetrafluoroborate.

Examples of sulfonium tetrafluoroborates are trimethylsulfonium, triethylsulfonium, dimethylethylsulfonium, diethylmethylsulfonium, dipropylmethylsulfonium, dipropylethylsulfonium, dibutylmethylsulfonium, di-sec-butylmethylsulfonium, dibutylethylsulfonium tetrafluoroborate. Very particular preference is given to the use of trimethylsulfonium and triethylsulfonium tetrafluoroborate.

A general scheme summarises the process according to the invention:

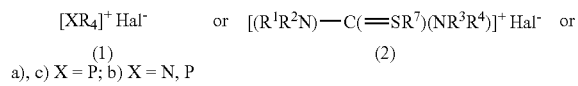

(1)
a), c) X = P; b) X = N, P

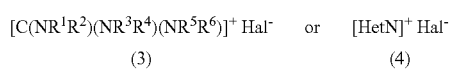

(3)      (4)

a) $[(alkyl)_3O]^+ [BF_4]^-$
or
+ b) $[(alkyl)_3S]^+ [BF_4]^-$
or
c) $[(phenyl)_3C]^+ [BF_4]^-$ -continued

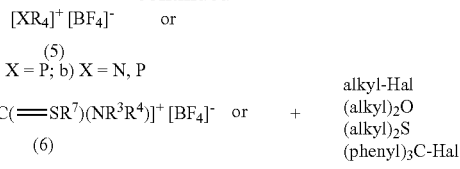

(5)
a), c) X = P; b) X = N, P

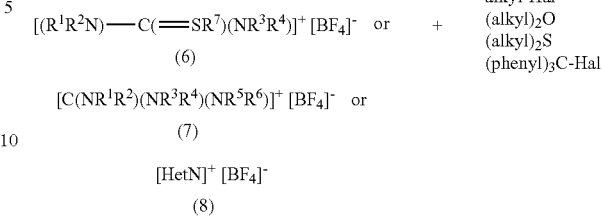

(6)

$[C(NR^1R^2)(NR^3R^4)(NR^5R^6)]^+ [BF_4]^-$ or
(7)

$[HetN]^+ [BF_4]^-$
(8)

The substituents R, $R^1$ to $R^7$ and HetN[+] of the compounds of the formulae (1) to (8) correspond to the meanings as described above.

In the case of reaction with trialkyloxonium tetrafluoroborate or triphenylcarbonium tetrafluoroborate, the reaction is carried out in accordance with the invention at temperatures between 0° and 100° C., preferably at 20° to 50°, particularly preferably at room temperature. In the case of reaction with sulfonium tetrafluoroborate, the reaction is carried out in accordance with the invention at temperatures between 0 and 150° C., preferably at 20 to 100° C. No solvent is required. However, it is also possible to employ solvents, for example dimethoxyethane, acetonitrile, dichloromethane, tetrahydrofuran, dimethyl sulfoxide, dioxane, propionitrile or mixtures with one another.

The reaction is carried out with an excess or equimolar amount of the corresponding oxonium tetrafluoroborate, sulfonium tetrafluoroborate or triphenylcarbonium tetrafluoroborate.

The method described is likewise suitable for the introduction of the anions $[(phenyl)_4B]^-$, $PF_6^-$, $SbF_6^-$ or $AsF_6^-$ into ionic liquids with onium cations by reacting alkyloxonium salts or alkylsulfonium salts with the corresponding anions with onium halides.

Even without further comments, it is assumed that a person skilled in the art will be able to utilise the above description in the broadest scope. The preferred embodiments and examples should therefore merely be regarded as descriptive disclosure which is absolutely not limiting in any way.

It goes without saying for the person skilled in the art that substituents in the compounds mentioned above and below, such as, for example, H, N, O, Cl, F, can be replaced by the corresponding isotopes.

The NMR spectra were measured on solutions in deuterated solvents at 20° C. on a Bruker ARX 400 spectrometer with a 5 mm $^1$H/BB broadband head with deuterium lock, unless indicated in the examples. The measurement frequencies of the various nuclei are: $^1$H, 400.13 MHz and $^{19}$F: 376.50 MHz. The referencing method is indicated separately for each spectrum or each data set.

EXAMPLES

Example 1

Synthesis of 1-hexyl-3-methylimidazolium tetrafluoroborate

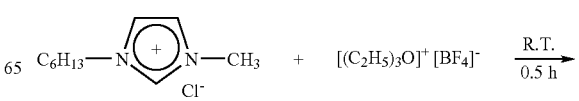

-continued

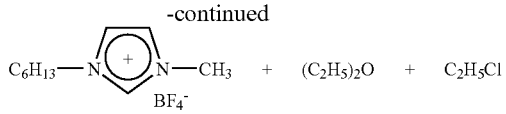

2.09 g (11.01 mmol) of triethyloxonium tetrafluoroborate are added to 2.21 g (10.90 mmol) of 1-hexyl-3-methylimidazolium chloride. The reaction mixture is stirred at room temperature for 30 minutes, and all volatile products are subsequently removed over the course of 30 minutes in a vacuum of 13.3 Pa and at 80° C. (temperature of the oil bath), giving 2.77 g of 1-hexyl-3-methylimidazolium tetrafluoroborate as liquid. The yield is approximately quantitative.

$^1$H NMR (reference: TMS; CD$_3$CN), ppm: 0.87 m (CH$_3$); 1.29 m (3CH$_2$); 1.81 m (CH$_2$); 3.82 s (CH$_3$); 4.11 t (CH$_2$); 7.34 d,d (CH); 7.38 d,d (CH); 8.47 br. s. (CH); $^3J_{H,H}$=7.1 Hz; $J_{H,H}$=1.8 Hz.

$^{19}$F NMR (reference: CCl$_3$F-internal; CD$_3$CN), ppm: −150.2 (BF$_4$).

Example 2

Synthesis of 1-cyano-4-dimethylaminopyridinium tetrafluoroborate

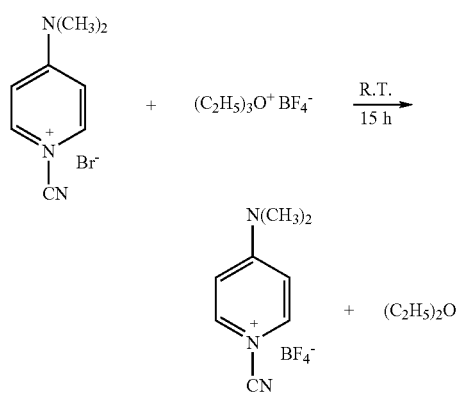

2.95 g (15.53 mmol) of triethyloxonium tetrafluoroborate in 10 ml of dry dichloromethane are added to a suspension of 2.13 g (9.34 mmol) of 1-cyano-4-dimethylaminopyridinium bromide in 5 ml of dry dichloromethane. The reaction mixture is stirred at room temperature for 15 hours. All volatile products are removed over the course of one hour in vacuo at 13.3 Pa and room temperature. The residue is taken up in 10 ml of dry acetonitrile, and 1-cyano-4-dimethylaminopyridinium tetrafluoroborate precipitates out on addition of 30 ml of ethyl acetate. The precipitate is filtered off and dried in vacuo at room temperature, giving 1.40 g of the solid. On partial distillation of the solvent, 0.39 g are again obtained. The yield of 1-cyano-4-dimethylaminopyridinium tetrafluoroborate is therefore together 1.79 g, corresponding to 81.6%.

$^1$H NMR (reference: TMS; CD$_3$CN), ppm 3.32 s (2CH$_3$), 6.98 d,m (2CH, A); 8.05 d,m (2CH, B); $^3J_{H(A),H(B)}$=8.1 Hz.

$^{19}$F NMR (reference: CCl$_3$F-internal; CD$_3$CN), ppm: −150.6 s (BF$_4$).

$^{13}$C NMR (reference: TMS; CD$_3$CN), ppm: 42.2 q,q [N(CH$_3$)$_2$]; 107.6 m (CN); 109.8 d,m (2CH); 141.5 d,m (2CH); 158.0 m (C); $^1J_{C,H}$=195 Hz; $^1J_{C,H}$=175 Hz; $^1J_{C,H}$=142 Hz; $^3J_{C,H}$=3.3 Hz.

Raman spectrum: 2266.7 cm$^{-1}$ (CN).

Elemental analysis C$_8$H$_{10}$BF$_4$N$_3$ (mol. weight 234.99):
found: C, 40.78%; H, 4.57%; N, 18.10%.
calculated: C, 40.89%; H, 4.29%; N, 17.88%.

Example 3

Analogously to Example 1,
1-methylimidazolium chloride is reacted with diethyloxonium tetrafluoroborate to give
  1-methylimidazolium tetrafluoroborate;
1-butylimidazolium chloride is reacted with diethyloxonium tetrafluoroborate to give
  1-butylimidazolium tetrafluoroborate;
1-ethyl-3-methylimidazolium chloride is reacted with diethyloxonium tetrafluoroborate to give
  1-ethyl-3-methylimidazolium tetrafluoroborate;
1-butyl-3-methylimidazolium chloride is reacted with diethyloxonium tetrafluoroborate to give
  1-butyl-3-methylimidazolium tetrafluoroborate;
1-methyl-3-pentylimidazolium chloride is reacted with diethyloxonium tetrafluoroborate to give
  1-methyl-3-pentylimidazolium tetrafluoroborate;
3-methyl-1-octylimidazolium chloride is reacted with diethyloxonium tetrafluoroborate to give
  3-methyl-1-octylimidazolium tetrafluoroborate;
1-decyl-3-methylimidazolium chloride is reacted with diethyloxonium tetrafluoroborate to give
  1-decyl-3-methylimidazolium tetrafluoroborate;
1-dodecyl-3-methylimidazolium chloride is reacted with diethyloxonium tetrafluoroborate to give
  1-dodecyl-3-methylimidazolium tetrafluoroborate;
3-methyl-1-tetradecylimidazolium chloride is reacted with diethyloxonium tetrafluoroborate to give
  3-methyl-1-tetradecylimidazolium tetrafluoroborate;
1-benzyl-3-methylimidazolium chloride is reacted with diethyloxonium tetrafluoroborate to give
  1-benzyl-3-methylimidazolium tetrafluoroborate;
3-methyl-1-phenylimidazolium chloride is reacted with diethyloxonium tetrafluoroborate to give
  3-methyl-1-phenylimidazolium tetrafluoroborate;
1-ethyl-2,3-dimethylimidazolium chloride is reacted with diethyloxonium tetrafluoroborate to give
  1-ethyl-2,3-dimethylimidazolium tetrafluoroborate;
1-butyl-2,3-dimethylimidazolium chloride is reacted with diethyloxonium tetrafluoroborate to give
  1-butyl-2,3-dimethylimidazolium tetrafluoroborate;
1-hexyl-2,3-dimethylimidazolium chloride is reacted with diethyloxonium tetrafluoroborate to give
  1-hexyl-2,3-dimethylimidazolium tetrafluoroborate or
1-hexyldecyl-2,3-dimethylimidazolium chloride is reacted with diethyloxonium tetrafluoroborate to give
  1-hexyldecyl-2,3-dimethylimidazolium tetrafluoroborate.

Example 4

Synthesis of 1-butylpyridinium tetrafluoroborate

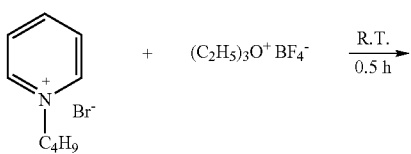

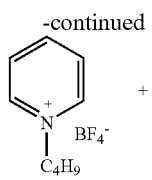 + (C₂H₅)₂O + C₂H₅Br 2.48 g (13.04 mmol) of triethyloxonium tetrafluoroborate are added to a solution of 2.77 g (12.82 mmol) of 1-butylpyridinium bromide in 10 ml of dry dichloromethane. The reaction mixture is stirred at room temperature for 30 minutes. All volatile products are subsequently removed over the course of 30 minutes in a vacuum of 13.3 Pa and at 80° C. (oil-bath temperature), giving 2.82 g of 1-butylpyridinium tetrafluoroborate as liquid. The yield is approximately quantitative.

¹H NMR (reference: TMS; CD₃CN), ppm: 0.95 t (CH₃); 1.37 m (CH₂); 1.95 m (CH₂); 4.54 t (CH₂); 8.04 m (2CH); 8.52 t,t (CH); 8.73 d (2CH); $^3J_{H,H}$=7.3 Hz; $^3J_{H,H}$=7.6 HZ; $^3J_{H,H}$=7.9 Hz; $^3J^{H,H}$=5.7 Hz; $^4J_{H,H}$=1.2 Hz.

¹⁹F NMR (reference: CCl₃F-internal; CD₃CN), ppm: −150.2 (BF₄).

Analogously thereto,
1-hexylpyridinium chloride is reacted with triethyloxonium tetrafluoroborate to give
  1-hexylpyridinium tetrafluoroborate;
1-butyl-4-methylpyridinium chloride is reacted with triethyloxonium tetrafluoroborate to give
  1-butyl-4-methylpyridinium tetrafluoroborate;
1-butyl-3-methylpyridinium bromide is reacted with triethyloxonium tetrafluoroborate to give
  1-butyl-3-methylpyridinium tetrafluoroborate or
1-butyl-3-ethylpyridinium bromide is reacted with triethyloxonium tetrafluoroborate to give
  1-butyl-3-ethylpyridinium tetrafluoroborate.

Example 5

Synthesis of 1-ethyl-1-methylpyrrolidinium tetrafluoroborate

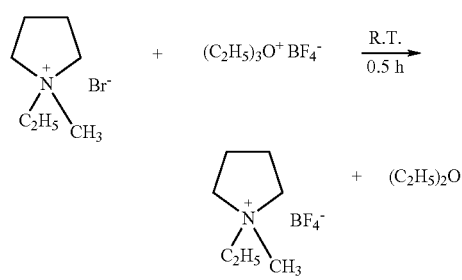

2.40 g (12.63 mmol) of triethyloxonium tetrafluoroborate are added to a solution of 2.45 g (12.62 mmol) of 1-ethyl-1-methylpyrrolidinium bromide in 10 ml of dry dichloromethane. The reaction mixture is stirred at room temperature for 30 minutes. All volatile products are subsequently removed over the course of 30 minutes in a vacuum of 13.3 Pa and at 80° C. (oil-bath temperature), giving 2.53 g of 1-ethyl-1-methylpyrrolidinium tetrafluoroborate. The yield is approximately quantitative.

¹H NMR (reference: TMS; CD₃CN), ppm: 1.31 t,m (CH₃); 2.13 m (2CH₂); 2.93 s (CH₃); 3.32 q (CH₂); 3.39 m (2CH₂); $^3J_{H,H}$=7.3 Hz.

¹⁹F NMR (reference: CCl₃F-internal; CD₃CN), ppm: −150.4 s (BF₄).

Analogously thereto,
1-butyl-1-methylpyrrolidinium chloride is reacted with triethyloxonium tetrafluoroborate to give
  1-butyl-1-methylpyrrolidinium tetrafluoroborate;
1-hexyl-1-methylpyrrolidinium chloride is reacted with triethyloxonium tetrafluoroborate to give
  1-hexyl-1-methylpyrrolidinium tetrafluoroborate;
1-methyl-1-octylpyrrolidinium chloride is reacted with triethyloxonium tetrafluoroborate to give
  1-methyl-1-octylpyrrolidinium tetrafluoroborate;
trihexyltetradecylphosphonium chloride is reacted with triethyloxonium tetrafluoroborate to give
  trihexyltetradecylphosphonium tetrafluoroborate.

Example 6

Synthesis of N,N,N',N'-tetramethyl-N''-ethylguanidinium tetrafluoroborate

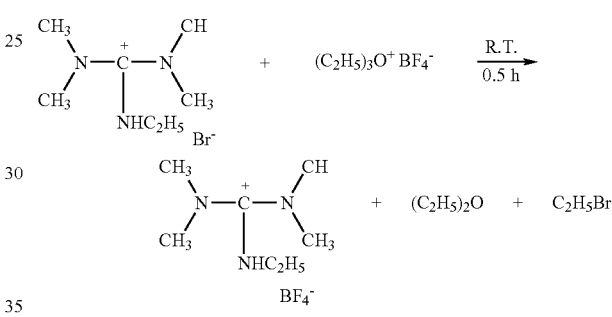

3.20 g (16.83 mmol) of triethyloxonium tetrafluoroborate are added to a solution of 3.73 g (16.64 mmol) of N,N,N',N'-tetramethyl-N''-ethylguanidinium bromide in 10 ml of dry dichloromethane. The reaction mixture is stirred at room temperature for 30 minutes. All volatile products are subsequently removed over the course of 30 minutes in a vacuum of 13.3 Pa and at 80° C. (oil-bath temperature), giving 3.84 g of N,N,N',N'-tetramethyl-N''-ethylguanidinium tetrafluoroborate. The yield is approximately quantitative.

¹H NMR (reference: TMS; CD₃CN), ppm: 1.11 t (CH₃); 2.86 brs; 2.87 br.s; 2.91 s (4CH₃); 3.20 m (CH₂); 6.17 br.s (NH); $^3J_{H,H}$=7.1 Hz.

¹⁹F NMR (reference: CCl₃F-internal; CD₃CN), ppm: −150.4 s (BF₄).

Example 7

Synthesis of Tetrabutylphosphonium Tetrafluoroborate

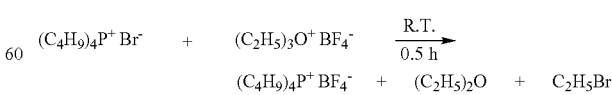

2.14 g (11.27 mmol) of triethyloxonium tetrafluoroborate are added to a solution of 3.81 g (11.23 mmol) of tetrabutylphosphonium bromide in 10 ml of dry dichloromethane. The reaction mixture is stirred at room temperature for 30 minutes. All volatile products are subsequently removed over the course of 30 minutes in a vacuum of 13.3 Pa and at 80° C. (oil-bath temperature), giving 3.88 g of tetrabutylphosphonium tetrafluoroborate. The yield is approximately quantitative.

$^1$H NMR (reference: TMS; CD$_3$CN), ppm: 0.94 t (CH$_3$); 1.47 m (2CH$_2$); 2.05 m (CH$_2$); $^3J_{H,H}$=7.1 Hz.

$^{19}$F NMR (reference: CCl$_3$F-internal, CD$_3$CN), ppm: −150.4 s (BF$_4$).

Example 8

Synthesis of 1-butyl-3-methylimidazolium tetrafluoroborate

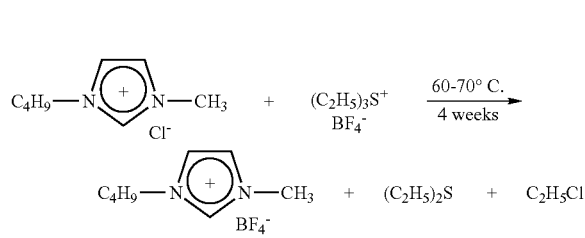

7.06 g (34.3 mmol) of triethylsulfonium tetrafluoroborate, (C$_2$H$_5$)$_3$S$^+$ BF$_4^-$, are added to 5.98 g (34.2 mmol) of solid 1-butyl-3-methylimidazolium chloride. The reaction mixture is stirred for a period of 4 weeks at 60-70° C. (temperature of the oil bath) and under an inert-gas atmosphere (nitrogen). All volatile products are pumped off over the course of 3 hours at a bath temperature of 70° C. and at a pressure of 13.3 Pa, giving 7.74 g of a liquid. The yield of 1-butyl-3-methylimidazolium tetrafluoroborate is virtually quantitative. The product obtained is investigated by means of NMR spectroscopy.

$^1$H NMR (reference: TMS; solvent: CD$_3$CN), ppm: 0.91 t (CH$_3$); 1.29 m (CH$_2$); 1.79 m (CH$_2$); 3.82 s (CH$_3$); 4.13 t (CH$_2$); 7.36 d,d (CH); 7.39 d,d (CH); 8.61 br, s. (CH); $^3J_{H,H}$=7.2 Hz; $J_{H,H}$=1.5 Hz.

$^{19}$F NMR (reference: CCl$_3$F-internal; solvent: CD$_3$CN), ppm: −150.1 (BF$_4$).

Example 9

Synthesis of 1-hexyl-3-methylimidazolium tetrafluoroborate

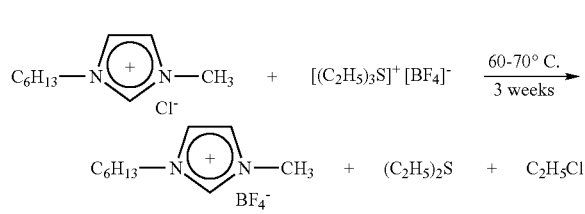

5.38 g (26.1 mmol) of triethylsulfonium tetrafluoroborate, (C$_2$H$_5$)$_3$S$^+$ BF$_4^-$, are added to 5.28 g (26 mmol) of liquid 1-hexyl-3-methylimidazolium chloride. The reaction mixture is stirred for a period of 3 weeks at 60-70° C. (temperature of the oil bath) and under an inert-gas atmosphere (nitrogen). All volatile products are pumped off over the course of 3 hours at a bath temperature of 70° C. and at a pressure of 13.3 Pa, giving 6.6 g of a liquid. The yield of 1-hexyl-3-methylimidazolium tetrafluoroborate is virtually quantitative. The product obtained is investigated by means of NMR spectroscopy.

$^1$H NMR (reference: TMS; solvent: CD$_3$CN), ppm: 0.87 m (CH$_3$); 1.29 m (3CH$_2$); 1.81 m (CH$_2$); 3.82 s (CH$_3$); 4.11 t (CH$_2$); 7.34 d,d (CH); 7.37 d,d (CH); 8.50 br. s. (CH); $^3J_{H,H}$=7.1 Hz; $J_{H,H}$=1.5 Hz.

$^{19}$F NMR (reference: CCl$_3$F-internal; solvent: CD$_3$ON), ppm: −150.2 (BF$_4$).

Example 10

Synthesis of 1-butylpyridinium tetrafluoroborate

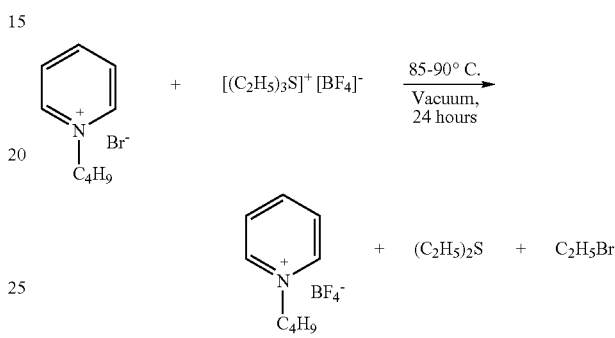

A mixture of 4.82 g (22.3 mmol) of N-butylpyridinium bromide and 4.62 g (22.4 mmol) of triethylsulfonium tetrafluoroborate, (C$_2$H$_5$)$_3$S$^+$ BF$_4^-$, is reacted over the course of 24 hours at 85-90° C. (temperature of the oil bath) at a dynamic pressure of 7 Pa. After cooling to room temperature, 4.97 g of an oil are obtained. The yield of N-butylpyridinium tetrafluoroborate is virtually quantitative. The product obtained is investigated by means of NMR spectroscopy.

$^1$H NMR (reference: TMS; solvent: CD$_3$CN), ppm: 0.93 t (CH$_3$); 1.35 m (CH$_2$); 1.95 m (CH$_2$); 4.58 t (CH$_2$); 8.05 m (2CH); 8.52 t,t (CH); 8.82 d (2CH); $^3J_{H,H}$=7.6 Hz; $^3J_{H,H}$=7.2 Hz; $J_{H,H}$=7.9 Hz; $J_{H,H}$=1.4 Hz.

$^{19}$F NMR (reference: CCl$_3$F-internal, solvent: CD$_3$CN), ppm: −150.1 (BF$_4$).

Example 11

Synthesis of S-ethyl-N,N,N',N'-tetramethylthiouronium tetrafluoroborate

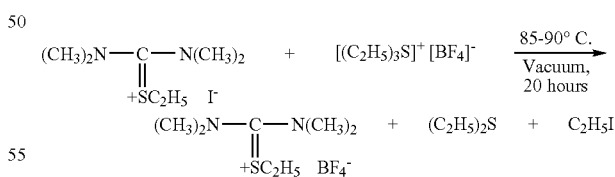

A mixture of 1.07 g (3.71 mmol) of S-ethyl-N,N,N',N'-tetramethylthiouronium iodide and 0.77 g (3.74 mmol) of triethylsulfonium tetrafluoroborate, (C$_2$H$_5$)$_3$S$^+$ BF$_4^-$, is reacted over the course of 20 hours at 85-90° C. (temperature of the oil bath) at a dynamic pressure of 7 Pa. After cooling to room temperature, 0.92 g of a solid are obtained. The yield of S-ethyl-N,N,N',N'-tetramethylthiouronium tetrafluoroborate is virtually quantitative. The melting point is 72-76° C. The product obtained is investigated by means of NMR spectroscopy.

$^1$H NMR (reference: TMS; solvent: CD$_3$CN), ppm: 1.31 t (CH$_3$); 3.01 q (CH$_2$); 3.23 s (4CH$_3$); $^3J_{H,H}$=7.4 Hz.

$^{19}$F NMR (reference: CCl$_3$F-internal; solvent: CD$_3$CN), ppm: –150.5 (BF$_4$).

Example 12

Synthesis of 1-hexyl-3-methylimidazolium tetrafluoroborate

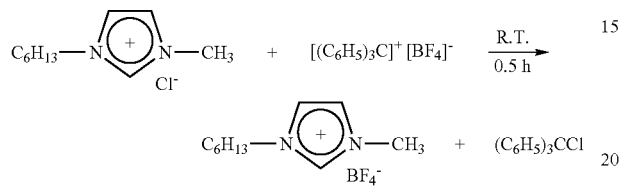

0.912 g (2.76 mmol) of triphenylcarbonium tetrafluoroborate, (C$_6$H$_5$)$_3$C$^+$ BF$_4^-$ and 5 cm$^3$ of benzene are added to 0.56 g (2.76 mmol) of 1-hexyl-3-methylimidazolium chloride. The reaction mixture is stirred at room temperature for 30 minutes. The upper (benzene) phase is separated off, and the product is washed three times with 10 ml of benzene. The residue is dried in vacuo at 13.3 Pa at a bath temperature of 100° C., giving 0.7 g of a liquid. The yield of 1-hexyl-3-methylimidazolium tetrafluoroborate is virtually quantitative. The product obtained is investigated by means of NMR spectroscopy.

$^1$H NMR (reference: TMS; solvent: CD$_3$CN), ppm 0.89 m (CH$_3$); 1.31 m (3CH$_2$); 1.82 m (CH$_2$); 3.84 s (CH$_3$); 4.11 m (CH$_2$); 7.36 d,d (CH); 7.39 d,d (CH); 8.50 br. s. (CH); $^3J_{H,H}$=7.2 Hz; $J_{H,H}$=1.7 Hz.

$^{19}$F NMR (reference: CCl$_3$F-internal; solvent: CD$_3$CN), ppm: –150.2 (BF$_4$)

The invention claimed is:

1. A process for preparing an onium tetrafluoroborate, comprising reacting an onium halide with a trialkyloxonium tetrafluoroborate, trialkylsulfonium tetrafluoroborate or triphenylcarbonium tetrafluoroborate, wherein the halide is of formula (4)

   (4)

where

Hal denotes Cl, Br or I, and

HetN$^+$ denotes a heterocyclic cation selected from the group consisting of

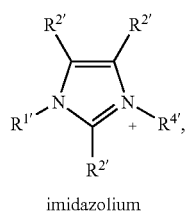

imidazolium

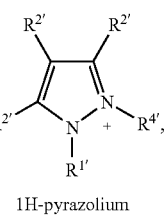

1H-pyrazolium

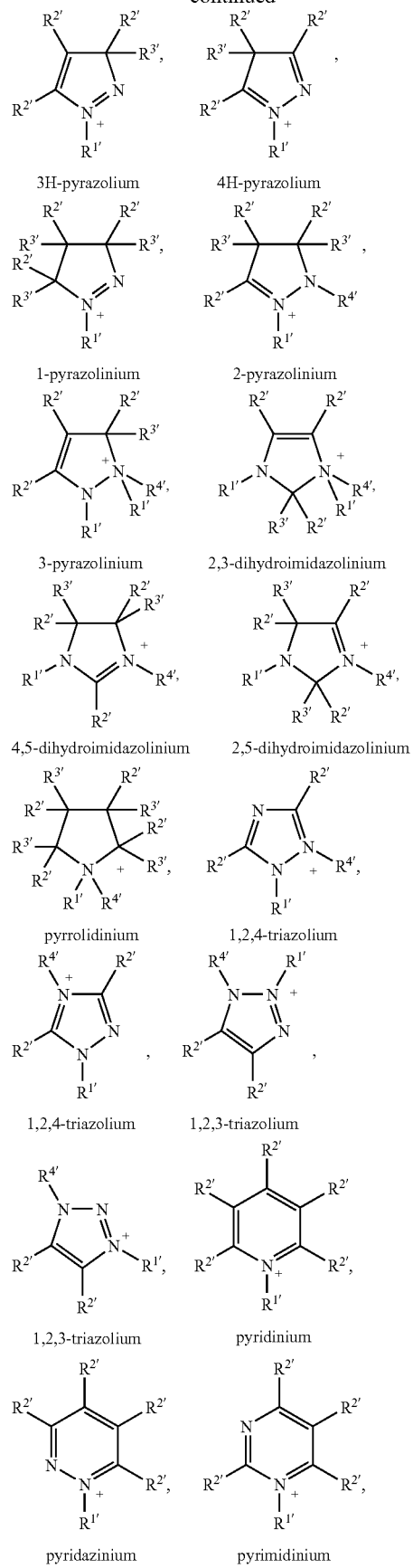

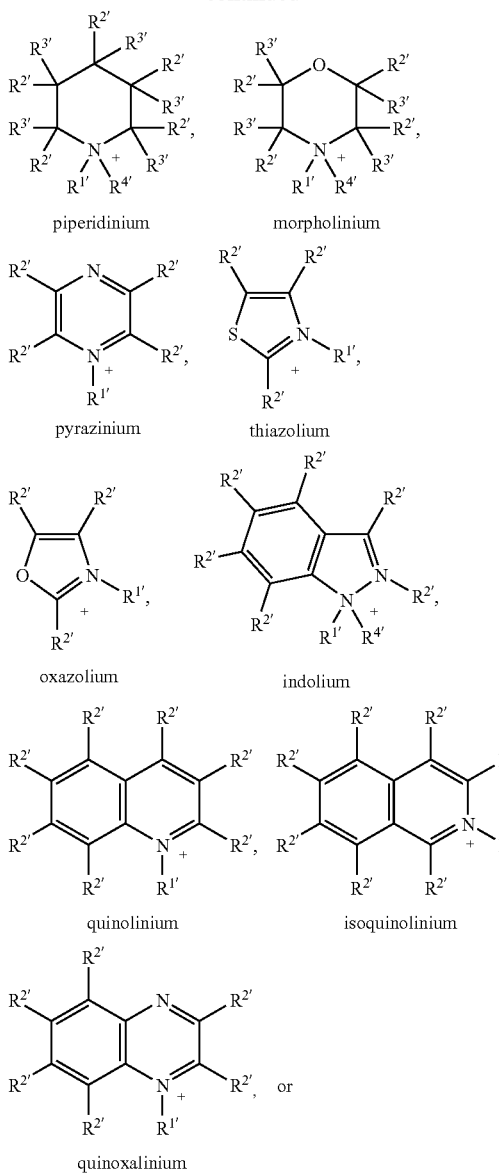
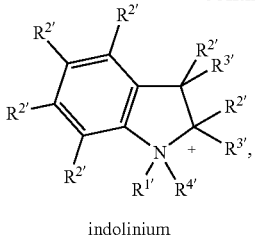

where
R¹' to R⁴' each, independently of one another, denotes
hydrogen or CN,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
dialkylamino having alkyl groups having 1-4 C atoms, but which is not bonded to the heteroatom of the heterocycle,
saturated, partially or fully unsaturated cycloalkyl having 3-7 C atoms, which may be substituted by one or more alkyl groups having 1-6 C atoms, or aryl-$C_1$-$C_6$-alkyl,
where the substituents R¹' and R⁴' may be partially or fully substituted by F, but where R¹' and R⁴' are not simultaneously CN or must not simultaneously be fully substituted by F,
where the substituents R²' and R³' may be partially or fully substituted by halogens or partially by $NO_2$ or CN, and
where, in the substituents R¹' to R⁴', one or two non-adjacent carbon atoms which are not bonded directly to the heteroatom and are not in the ω-position may be replaced by atoms and/or atom groups —O—, —S—, —S(O)— or —$SO_2$—.

2. A process according to claim 1, wherein an oxonium tetrafluoroborate is reacted.

3. A process according to claim 1, wherein, in the case of reaction with trialkyloxonium tetrafluoroborate or triphenylcarbonium tetrafluoroborate, the reaction is carried out at temperatures between 0° and 100° C. and, in the case of reaction with sulfonium tetrafluoroborate, the reaction is carried out at temperatures between 0 and 150° C.

* * * * *

UNITED STATES PATENT AND TRADEMARK OFFICE
CERTIFICATE OF CORRECTION

| | | |
|---|---|---|
| PATENT NO. | : 8,101,749 B2 | Page 1 of 1 |
| APPLICATION NO. | : 11/721613 | |
| DATED | : January 24, 2012 | |
| INVENTOR(S) | : Nikolai Mykola Ignatyev et al. | |

It is certified that error appears in the above-identified patent and that said Letters Patent is hereby corrected as shown below:

Column 21, Line 43 after the structure reads: "or" should read --and--.

Signed and Sealed this
Tenth Day of April, 2012

David J. Kappos
*Director of the United States Patent and Trademark Office*